(12) United States Patent
Palmer (10) Patent No.: US 8,746,080 B2
(45) Date of Patent: Jun. 10, 2014

(54) COMPACT AND ROBUST LOAD AND MOMENT SENSOR

(75) Inventor: Michael L. Palmer, Ladera Ranch, CA (US)

(73) Assignee: Freedom Innovations, L.L.C., Irvine, CA (US)

( * ) Notice: Subject to any disclaimer, the term of this patent is extended or adjusted under 35 U.S.C. 154(b) by 293 days.

(21) Appl. No.: 13/015,423

(22) Filed: Jan. 27, 2011

(65) Prior Publication Data

US 2011/0197682 A1   Aug. 18, 2011

Related U.S. Application Data

(60) Provisional application No. 61/304,367, filed on Feb. 12, 2010.

(51) Int. Cl.
*G01L 1/22* (2006.01)

(52) U.S. Cl.
USPC .................................................. 73/862.045

(58) Field of Classification Search
CPC ........... A61F 2/64; A61F 2/6607; A61F 2/76; A61F 2002/7635; A61F 2002/7645; G01L 5/161
USPC ........................ 73/862.045; 600/595; 606/102
See application file for complete search history.

(56) References Cited

U.S. PATENT DOCUMENTS

| | | | |
|---|---|---|---|
| 5,190,126 A | 3/1993 | Curnutt | |
| 6,978,872 B2 | 12/2005 | Turner | |
| 2001/0029400 A1 | 10/2001 | Deffenbaugh et al. | |
| 2002/0139203 A1 | 10/2002 | Chimura et al. | |
| 2003/0033885 A1 | 2/2003 | Knox et al. | |
| 2005/0154473 A1 | 7/2005 | Bassett | |
| 2006/0136072 A1 | 6/2006 | Bisbee, III et al. | |
| 2007/0050044 A1 | 3/2007 | Haynes et al. | |
| 2007/0228500 A1 | 10/2007 | Shimazu et al. | |
| 2007/0255424 A1 | 11/2007 | Leydet et al. | |
| 2008/0139970 A1* | 6/2008 | Macomber et al. | 600/595 |
| 2008/0154156 A1 | 6/2008 | Dellon et al. | |
| 2008/0295610 A1 | 12/2008 | Inamori | |
| 2009/0031822 A1 | 2/2009 | Ohta et al. | |

OTHER PUBLICATIONS

Sup, Frank et al., "Design and Control of a Powered Transfemoral Prosthesis", The International Journal of Robotics Research, 2008, pp. 263-273, http://ijr.sagepub.com/cgi/content/abstract/27/2/263.
PCT Application No. PCT/US2011/022752 International Search Report and Written Opinion, dated Sep. 1, 2011, 10 pages.
PCT Application No. PCT/US2011/022750 International Search Report and Written Opinion, dated Oct. 24, 2011, 9 pages.

\* cited by examiner

*Primary Examiner* — Lisa Caputo
*Assistant Examiner* — Brandi N Hopkins
(74) *Attorney, Agent, or Firm* — Snell & Wilmer LLP (57) ABSTRACT

The present invention relates to a load and moment sensor for a prosthetic device detecting load in a single direction and moment in a single plane. The load and moment sensor includes a sensing element, and a plurality of strain gauges placed in specific locations of the sensing element. The plurality of strain gauges is part of a plurality of resistor circuits such as Wheatstone bridges. While the strain gauges can be located on a single sensing element, some resistive elements of the Wheatstone bridges can be located elsewhere on the prosthetic device. The combination of the location of the strain gauges and the use of the Wheatstone bridges allows for good side load rejection which is load and moment not in the single direction or the single plane.

18 Claims, 9 Drawing Sheets

COMPACT AND ROBUST LOAD AND MOMENT SENSOR

CROSS-REFERENCES TO RELATED APPLICATIONS

The present application claims the benefit of U.S. Provisional Application Ser. No. 61/304,367 filed on Feb. 12, 2010 entitled: "Compact and Robust Load and Moment Sensor," which is hereby incorporated by reference in its entirety. The present application also incorporates by reference U.S. Pat. No. 7,655,050 and U.S. application Ser. No. 12/697,969, filed Feb. 1, 2010, each as if fully set forth herein.

BACKGROUND

1. Field of the Invention

This disclosure relates to sensors for detecting loads and moments applied to the sensor, and more specifically to a compact and robust sensor for detecting loads applied to the sensor in a single direction and moments applied to the sensor in a single plane.

2. Description of the Related Art

Modern, computer-controlled prosthetic devices have many advantages over conventional prosthetic devices. For example, computer-controlled prosthetic devices can allow the amputees to walk with limited fear of stumbling or falling, allow amputees to lead a more active lifestyle, and improve the likelihood that amputees can realize their full economic potential. It is desirable to extend these benefits to as many as is possible of the thousands of new amputees each year, and the millions of existing amputees.

A load and moment sensor that is both compact and robust would extend the benefits of the modern, computer-controlled prosthetic device to a broader cross section of the amputee population. Since the prosthetic device must be the same length as the intact limb of the amputee, a more compact sensor allows the prosthetic device to be used by amputees that are shorter in height, especially children. Furthermore, a more robust sensor allows the prosthetic device to be used both in harsher environments and in more aggressive activities such as construction, hiking, and various sports.

In addition, designing a single, compact sensor to measure both an applied load and an applied moment presents a difficult challenge. The need to have a usable load output and the need to have a compact sensor may be opposing requirements. For example, when a force is applied to the sensor at a point off center, it typically generates not only an applied load on the sensor, but also an applied moment on the sensor. The applied load and moment create strains in the sensor. As the force is shifted further off center, the strain induced by the applied moment increases while the strain induced by the applied load remains constant. At a certain point, the strain induced by the applied load will be so small relative to the strain induced by the applied moment that it will become very difficult to measure both strains in the same sensor. One solution to maintain balance between load-induced strain and moment-induced strain is to increase the physical size of the sensor in the plane of the applied moment thereby sacrificing compactness.

Thus, there is a need for a compact and robust load and moment sensor for detecting loads applied to the sensor in a single direction and moments applied to the sensor in a single plane.

SUMMARY

The present invention relates to a compact and robust load and moment sensor for detecting loads applied to the sensor in a single direction and moments applied to the sensor in a single plane. This allows for load and moment detection in a compact sensor which can be modular. The modularity of the load and moment sensor allows for it to be replaced easily if it is damaged. Furthermore, the modularity allows for the load and moment sensor to be formed from a high strength material such as steel with minimal impact on the device's overall weight. The high strength material can improve the functional life of the load and moment sensor.

The load and moment sensor of the present invention includes a plurality of strain gauges placed on specific locations of a sensing element of the sensor. The plurality of strain gauges are wired together into resistor circuits such as two Wheatstone bridges. The output of one Wheatstone bridge is proportional to the applied load while the output of the other is proportional to the applied moment. While the strain gauges can be located, for example, on a single sensing element, some of the resistive elements of the Wheatstone bridges can be located elsewhere on the prosthetic leg. By intelligently placing the strain gauges on the single sensing element, and by using the Wheatstone bridges, more accurate information regarding the load in the single direction and the load in the single plane is received. That is, the combination of the location of the strain gauges and the use of the Wheatstone bridges allows for good side load rejection (which is load and/or moment not in the single direction or the single plane), good noise rejection, and good temperature compensation.

The good side load rejection, noise rejection, and temperature compensation can allow the prosthetic leg to more accurately mimic a human gait. Furthermore, the use of one Wheatstone bridge for applied load and another for applied moment improves performance of the prosthetic leg since a processor does not need to calculate the load and moment. The load and moment are measured directly from the outputs of the Wheatstone bridges.

In addition, the use of a single sensing element can reduce an amount of components utilized by the prosthetic leg. Since components are prone to be damaged, reducing a number of components also reduces an amount of objects which can be potentially damaged. This translates to a lower cost and greater reliability because there are less components that are prone to being damaged and which need to be replaced.

Also, the strain gauges can be semiconductor strain gauges which tend to have a smaller size while having a higher gauge factor. The higher gauge factor allows for the load and moment sensor to provide accurate results using low strains, which increases fatigue life and resistance to overloading of the load and moment sensor.

These improvements in the sensor can improve the functionality of the prosthetic leg such that it may have application to a broader cross section of the amputee population. The compact feature of the load and moment sensor of the present invention allows the prosthetic device to be used by amputees that are shorter in height, especially children, since the prosthetic device must be the same length as the intact limb of the amputee. Furthermore, the robustness of the load and moment sensor of the present invention allows the prosthetic device to be used both in harsher environments and in more aggressive activities such as construction, hiking, and various sports.

In one embodiment, the present invention is a load and moment sensor including a sensing element, a first Wheatstone bridge including a first plurality of strain gauges located on the sensing element, wherein the first Wheatstone bridge detects a moment in a single plane, and a second Wheatstone bridge including a second plurality of strain gauges located on the sensing element, wherein the second Wheatstone bridge detects a load in a single direction.

In another embodiment, the present invention is a load and moment sensor including a sensing element including a mounting surface, a first Wheatstone bridge including a first strain gauge, a second strain gauge, a third strain gauge, and a fourth strain gauge, wherein the first strain gauge, the second strain gauge, the third strain gauge, and the fourth strain gauge are located on the sensing element in a first plane parallel to the mounting surface, and the first Wheatstone bridge detects a moment in a single plane. The load and moment sensor can also include a second Wheatstone bridge including a fifth strain gauge, a sixth strain gauge, a seventh strain gauge, and an eighth strain gauge, wherein the fifth strain gauge, the sixth strain gauge, the seventh strain gauge, and the eighth strain gauge are located on the sensing element in a second plane perpendicular to the mounting surface, and the second Wheatstone bridge detects a load in a single direction.

In yet another embodiment, the present invention is a method for determining a load and a moment applied to a load and moment sensor including using a first set of strain gauges located on a sensing element to measure a moment applied to the load and moment sensor, and using a second set of strain gauges located on the sensing element to measure a load applied to the load and moment sensor.

BRIEF DESCRIPTION OF THE DRAWINGS

The above-mentioned features and objects of the present disclosure will become more apparent with reference to the following description taken in conjunction with the accompanying drawings wherein like reference numerals denote like elements and in which.

DETAILED DESCRIPTION

The detailed description of exemplary embodiments herein makes reference to the accompanying drawings and pictures, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

As seen in FIGS. 1-5, a load and moment sensor 100 can include a sensing element 102. The load and moment sensor 100 can be compact and robust and can measure both an applied load in a single direction and an applied moment in a single plane.

Figure 4:
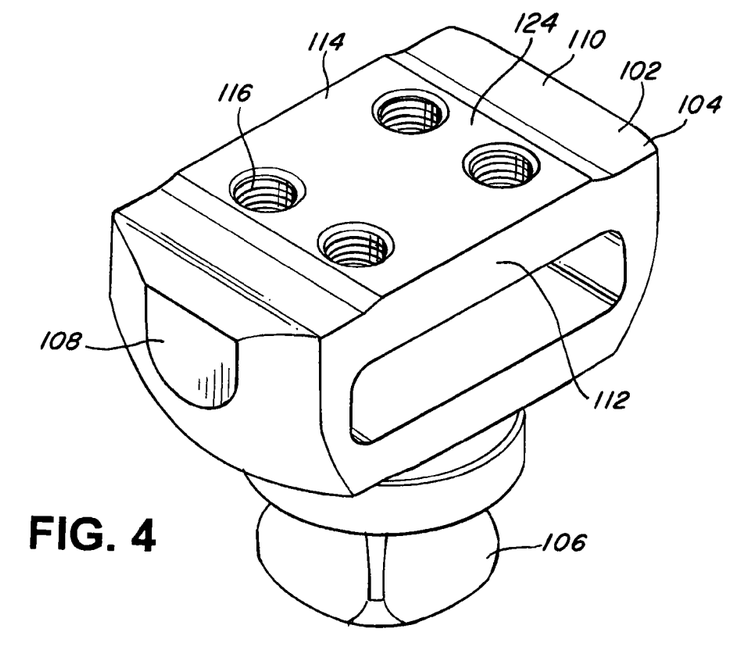
FIG. 4 is a perspective view of a load and moment sensor according to an embodiment of the present invention.
Figure 5:
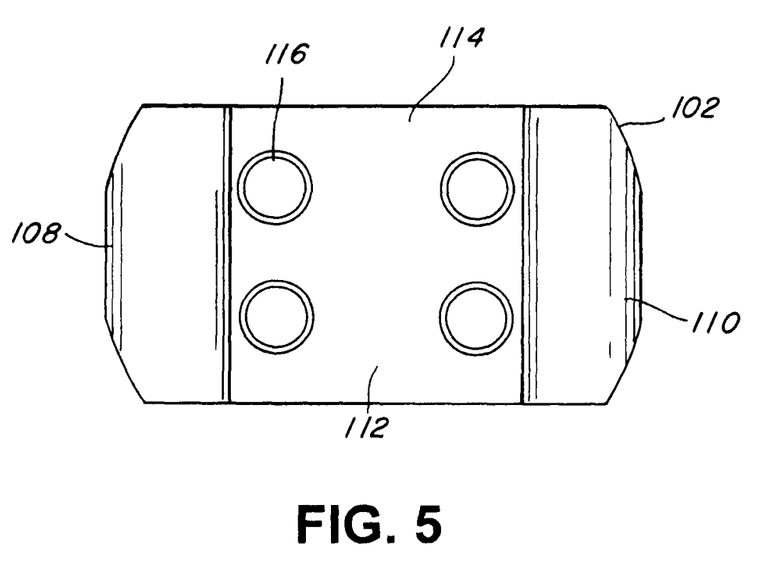
FIG. 5 is a top view of a load and moment sensor according to an embodiment of the present invention.

The sensing element 102 can include, for example, a top portion 104, a bottom portion 106, a front side 108, a back side 110, a first side 112, and a second side 114 (FIG. 4). In one embodiment, the first side 112 is a right side, while the second side 114 is a left side. The sensing element 102 can also include, for example, a mounting surface 124. As seen in FIG. 4, the mounting surface 124 can include, for example, a plurality of holes 116. The plurality of holes 116 can be, for example, threaded holes which are configured to receive threaded fasteners.

In one embodiment, the threaded fasteners (not shown) are used in conjunction with the holes 116 to mount the mounting surface 124 of the sensing element 102 to a portion of a prosthetic device such as a prosthetic ankle and/or a knee. The threaded fasteners can create large amounts of friction to hold the sensing element 102 in place and to also add stiffness to the joint between the sensing element 102 and the surface of the prosthetic device. At the same time, the threaded fasteners are located relatively far away from the strain gauges (described below). Therefore, if there is movement between the sensing element 102 and the prosthetic device, that movement does not induce strain in the sensing element 102 in the region of the strain gauges. This allows the sensing element 102 and the load and moment sensor 100 to withstand large side loads, including side loads due to impact, without a change to the no-load output of the load and moment sensor 100.

The load and moment sensor 100 is designed to be modular in that it can be mounted to a prosthetic device in a way that it can be easily replaced if it is damaged. Furthermore, this modularity of the load and moment sensor 100 allows the sensing element 102 to be made from a high strength material or high strength steel with minimal impact on the overall weight of the prosthetic device. For example, the sensing element 102 can be formed from metal and/or a carbon fiber material. In one embodiment, the sensing element 102 is machined from a solid piece of AISI 630 (17-4 PH) stainless steel and then heat treated to condition H900. This material and heat treatment gives the sensing element 102 high strength and good corrosion resistance for harsh environments. At the same time, this material has a good "memory" meaning that it tends to return to the original state of strain after a load is applied then removed. This results in the load and moment sensor 100 providing a more stable output.

Figure 1:
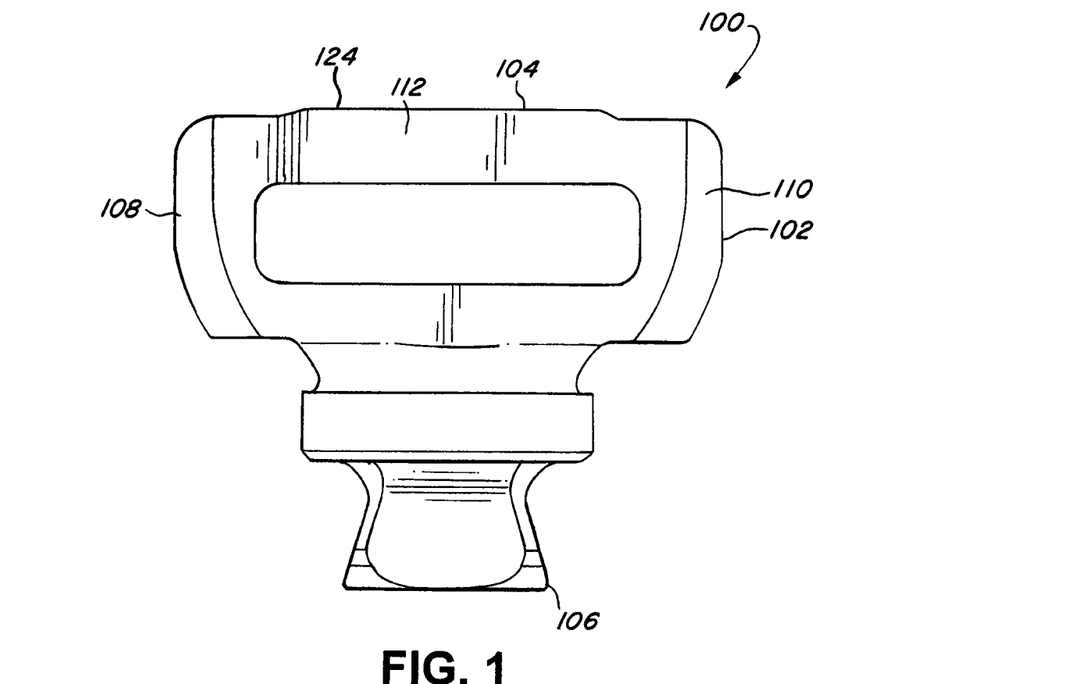
FIG. 1 is a side view of a load and moment sensor according to an embodiment of the present invention.
Figure 2:
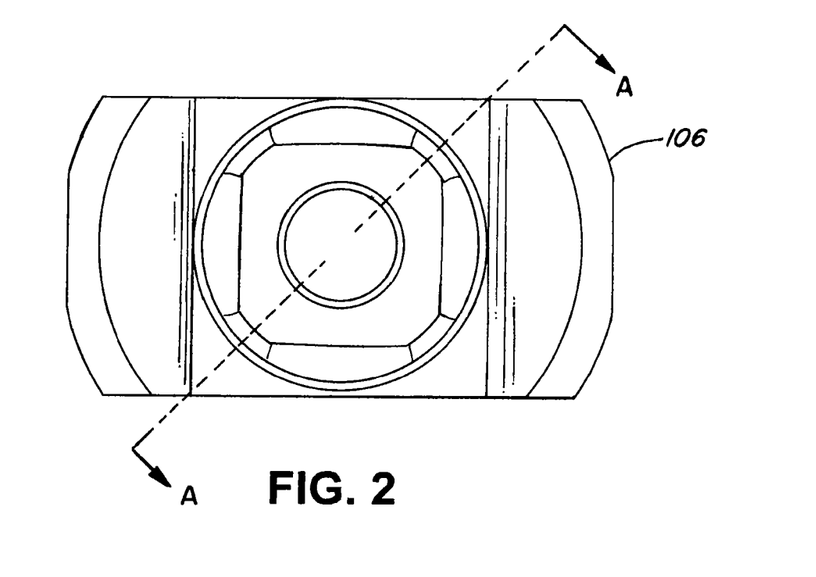
FIG. 2 is a bottom view of a load and moment sensor according to an embodiment of the present invention.
Figure 3:
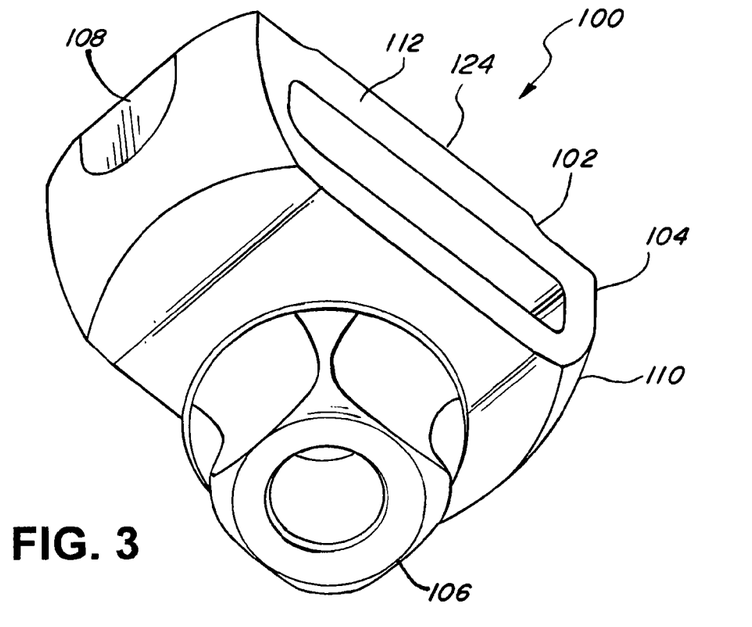
FIG. 3 is a perspective view of a load and moment sensor according to an embodiment of the present invention.
Figure 6:
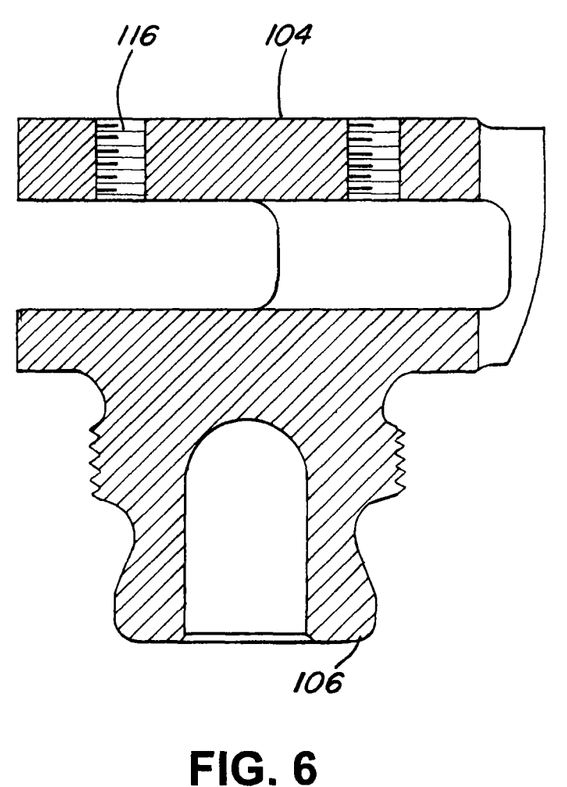
FIG. 6 is a sectional view of a load and moment sensor according to an embodiment of the present invention.
Figure 7:
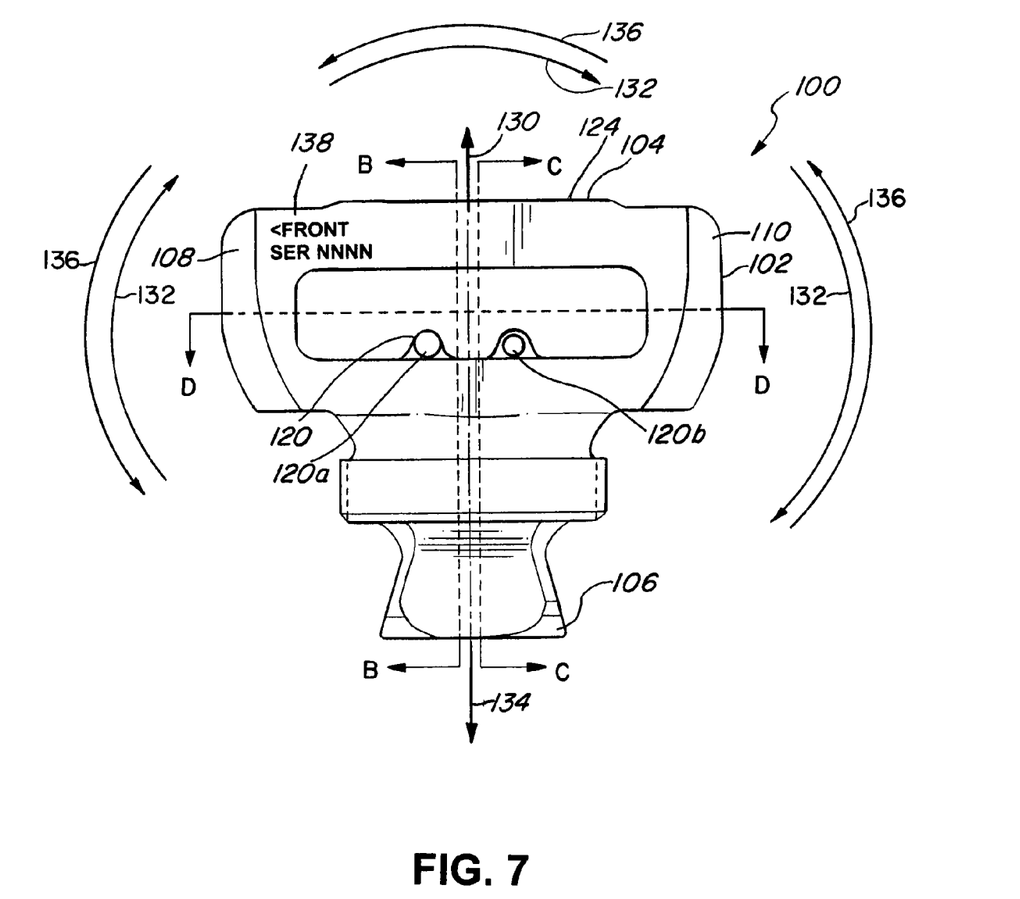
FIG. 7 is a side view of a load and moment sensor according to an embodiment of the present invention.

FIG. 6 depicts a portion of the sensing element 102 along the cross-section A-A of FIG. 2. FIG. 6 depicts, for example, the plurality of holes 116. As seen in FIG. 7, the load and moment sensor 100 can also include, for example, lead wires 120 located on the sensing element 102 which can be connected to the strain gauges (described below) to carry an output of the strain gauges. In one embodiment, the lead wires 120 can include, for example, the lead wires 120a and 120b. In addition, the load and moment sensor 100 can also include indicia 138 which can indicate, for example, the location of the front side 108 of the load and moment sensor 100. The indicia can also include, for example, a serial number of the load and moment sensor 100 for quality control purposes. Furthermore, the indicia can also include additional information which may be useful to the installation, quality control, or operation of the load and moment sensor 100.

Figure 8:
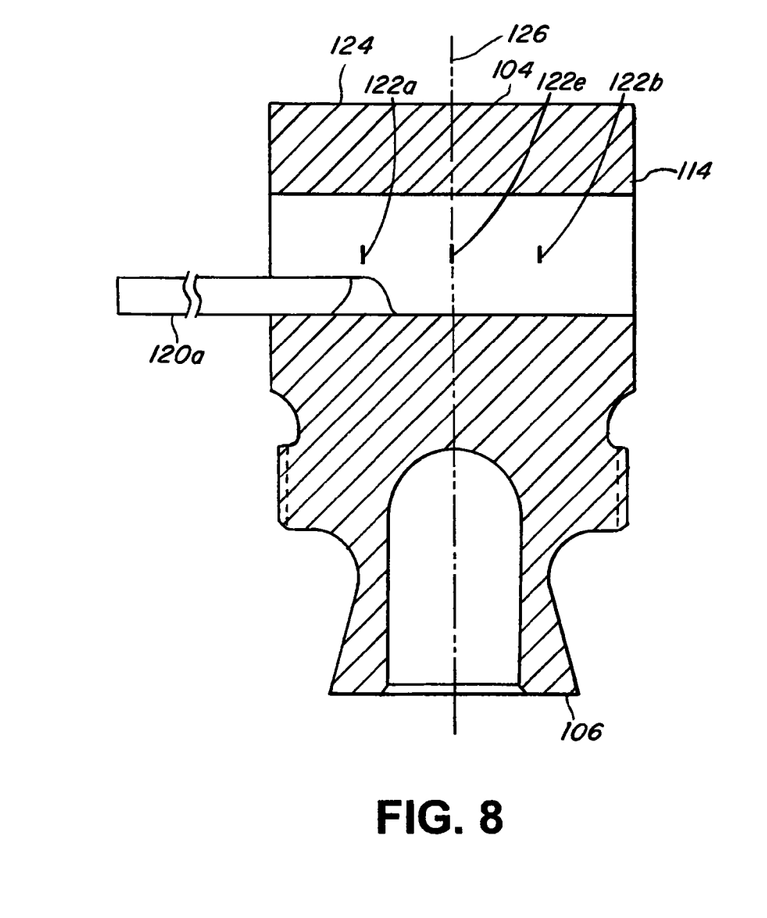
FIG. 8 is a sectional view of a load and moment sensor according to an embodiment of the present invention.
Figure 9:
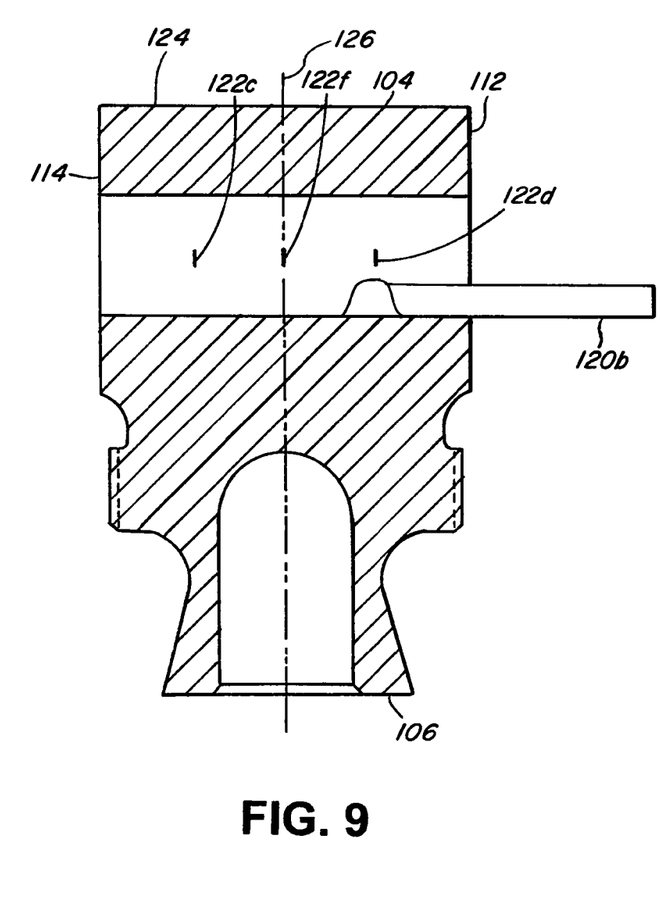
FIG. 9 is a sectional view of a load and moment sensor according to an embodiment of the present invention.
Figure 10:
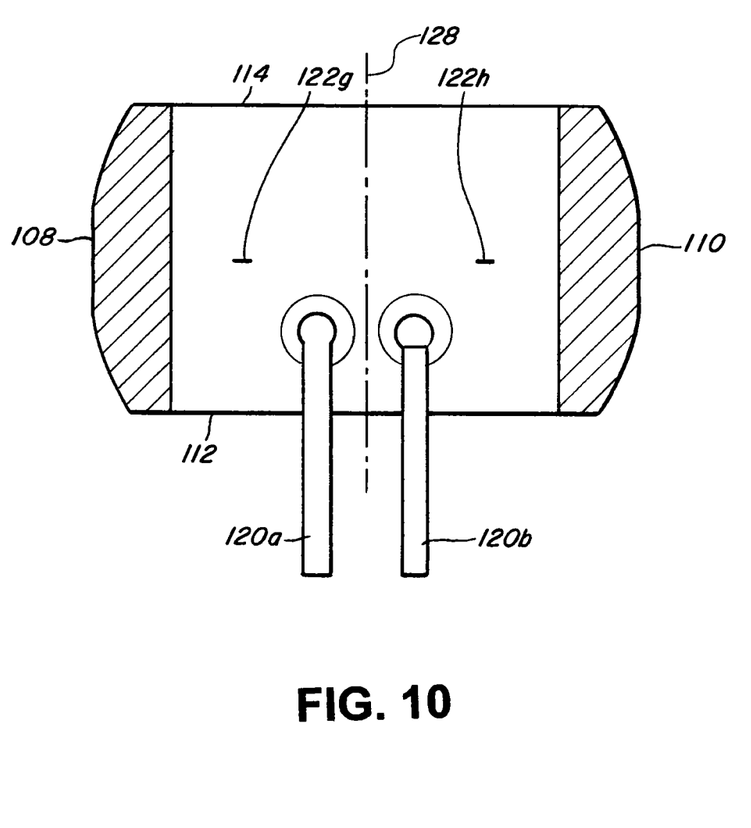
FIG. 10 is a sectional view of a load and moment sensor according to an embodiment of the present invention.

In one embodiment, as seen in FIG. 8 (cross-section of FIG. 7 along the line B-B), FIG. 9 (cross-section of FIG. 7 along the line C-C), and FIG. 10 (cross-section of FIG. 7 along the line D-D), the strain gauges 122a, 122b, 122c, and 122d are used, for example, to detect a moment in a single plane, while the strain gauges 122e, 122f, 122g, and 122h are used, for example, to detect a load in a single direction. Thus, the strain gauges 122a-122d can provide an output that represent a magnitude of a moment applied to the load and moment sensor 100 in a single plane, while the strain gauges 122e-122h can provide an output that represent a magnitude of a load applied to the load and moment sensor 100 in a single direction.

In one embodiment, the strain gauges 122a-122h are bonded to the sensing element 102 using standard industry practices. In a preferred embodiment, the strain gauges 122a-122h are bonded to only a single sensing element 102. In addition, the use of the single sensing element 102 can reduce an amount of components utilized by the prosthetic device. Since components are prone to be damaged, reducing a number of components also reduces an amount of objects which can be potentially damaged. This translates to a lower cost and greater reliability because there are fewer components that are prone to being damaged and which need to be replaced.

Also, the strain gauges can be semiconductor strain gauges which tend to have a smaller size while having a higher gauge factor. The higher gauge factor allows for the load and moment sensor to provide accurate results using low strains, which increases fatigue life and resistance to overloading of the load and moment sensor.

The strain gauges 122a-122h can be a variety of type of strain gauges such as metal foil, semiconductor, or other types of strain gauges. Semiconductor strain gauges are preferably used due to their small size, and their advantage of having a gauge factor in the range of 100-155. This is two orders of magnitude greater than that of metal foil gauges which often have gauge factors of 2-5. The high gauge factor of the semiconductor strain gauges results in both a more robust sensor and a higher voltage output. The robustness comes from the fact that less strain is required to achieve a usable output, and the higher voltage output is less susceptible to noise. This improves the accuracy of the information output by the semiconductor strain gauges, which results in the load and movement sensor 100 being more accurate. The improved accuracy of the load and moment sensor 100 allows the prosthetic leg to more accurately mimic a human gait.

Figure 11:
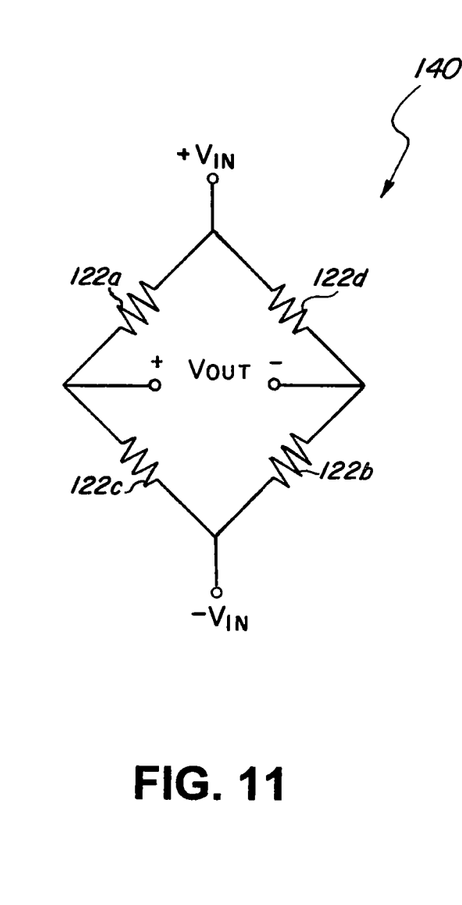
FIG. 11 depicts a Wheatstone bridge according to an embodiment of the present invention.
Figure 12:
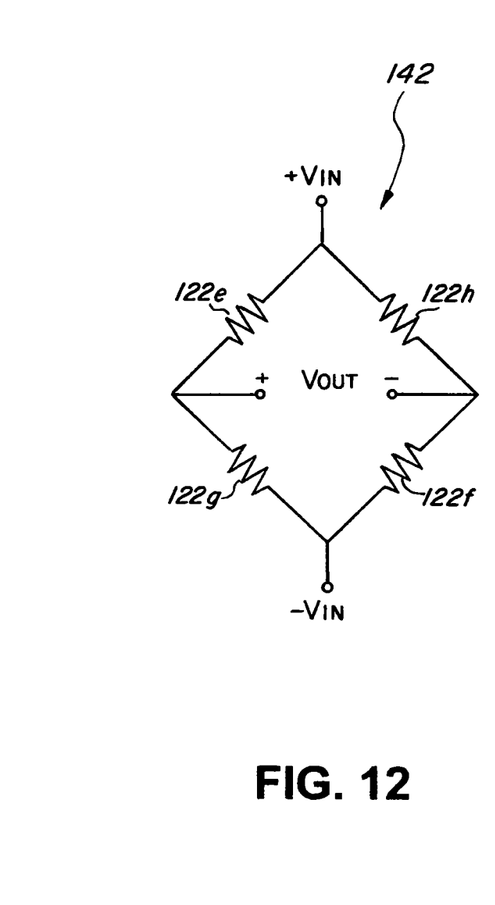
FIG. 12 depicts a Wheatstone bridge according to an embodiment of the present invention.

To detect the moment in a single plane and the load in a single direction, the strain gauges 122a-122h can be part of resistor circuits, such as a first Wheatstone bridge 140 and a second Wheatstone bridge 142 as shown in FIGS. 11 and 12, respectively. The strain gauges 122a-122h can function as variable resistors in the two Wheatstone bridge circuits. When the strain gauges 122a-122h experience compressive strain, their electrical resistance is decreased. When the strain gauges 122a-122h experience tensile strain, their electrical resistance is increased. The use of the Wheatstone bridges improves performance of the prosthetic leg since a processor does not need to calculate the load and moment. The output of the Wheatstone bridges can correlate with the amount and direction of the applied load or moment.

The output of the first Wheatstone bridge 140 is proportional to the applied moment in a single plane perpendicular to the mounting surface 124 (FIG. 1) and the output of the second Wheatstone bridge 142 is proportional to the applied load along a single axis perpendicular to the mounting surface 124. While the strain gauges 122a-122h (FIGS. 10-12) are located on the sensing element 102, some of the resistive elements of the first Wheatstone bridge 140 and the second Wheatstone bridge 142 need not be located on the sensing element 102 (FIG. 1), instead some of the resistive elements of the first Wheatstone bridge 140 and the second Wheatstone bridge 142 can be placed in a different location, such as on the prosthetic leg, ankle or joint that the sensing element 102 (FIG. 1) is attached to.

As seen in FIG. 11, the first Wheatstone bridge 140 can include, for example, the strain gauges 122a-122d. In order for the first Wheatstone bridge 140 to generate a positive moment output, the moment has to be applied in a direction 132 which lies in a single plane perpendicular to the mounting surface 124 as shown in FIG. 7. The applied moment can be detected by the strain gauges 122a-122d. The applied moment in the direction 132 would cause the load and moment sensor 100 to rotate in a clockwise direction when viewed from the first side 112 if the load and moment sensor 100 was not mounted. To generate a negative moment output, the moment has to be applied in a direction 136 which lies in the single plane perpendicular to the mounting surface 124. The applied moment in the direction 136 would cause the load and moment sensor 100 to rotate in a counter-clockwise direction when viewed from the first side 112 if the load and moment sensor 100 was not mounted.

Referring to FIG. 7, FIG. 8 (cross section of FIG. 7 along the line BB), and FIG. 9 (cross section of FIG. 7 along the line C-C), when a moment is applied, for example, in the direction 132 (FIG. 7) shown for a positive moment, the strain gauge 122a and the strain gauge 122b (FIG. 8) experience compressive strain while the strain gauge 122c and the strain gauge 122d (FIG. 9) experience tensile strain. The compressive strain experienced in the strain gauges 122a and 122b decreases their electrical resistance, while the tensile strain experienced in the strain gauges 122c and 122d increases their electrical resistance.

Referring back to FIG. 11, since the strain gauges 122a (decreased electrical resistance) and 122c (increased electrical resistance) are paired on a first side of the first Wheatstone bridge 140, a first voltage can be outputted. Since the strain gauges 122b (decreased electrical resistance) and 122d (increased electrical resistance) are paired on a second side of the first Wheatstone bridge 140, in an opposite configuration, a second voltage can be outputted. Due to the opposite configuration, the second voltage has the same magnitude as the first voltage, but has a different polarity. This results in a positive voltage differential between the first voltage and the second voltage, and subsequently a positive voltage output.

Of course, the first Wheatstone bridge 140 could also be configured to generate a positive moment output in the direction 136 and a negative load output in the direction 132. Although four strain gauges are shown in FIG. 11, two or more strain gauges can be used instead. In such a case, other types of resistors, having a fixed or variable resistance, can be used to replace the strain gauges, and the strain gauges can be arranged into circuits other than a Wheatstone bridge such as a half bridge or voltage divider.

Likewise, the second Wheatstone bridge 142 in FIG. 12 can include, for example, the strain gauges 122e-122h. In order for the second Wheatstone bridge 142 to generate a positive load output, the load has to be applied to the load and moment sensor 100 in a direction 130 perpendicular to the mounting surface 124 as shown in FIG. 7. The strain gauges 122e-122h can detect the applied load. When the load is applied to the load and moment sensor 100 in a direction 134, a negative load output is generated.

Referring to FIGS. 7-10, when the load is applied, for example, in the direction 130 (FIG. 7) shown for a positive load, the strain gauges 122e and 122f (FIGS. 8 and 9) experience compressive strain while the strain gauges 122g and 122h (FIG. 10) experience tensile strain. The compressive strain experienced in the strain gauges 122e and 122f decreases their electrical resistance, while the tensile strain experienced in the strain gauge 122g and 122h increases their electrical resistance. Since the strain gauges 122e (decreased electrical resistance) and 122g (increased electrical resistance) are paired on a first side of the second Wheatstone bridge 142 (FIG. 12), a third voltage can be outputted. Since the strain gauges 122f (decreased electrical resistance) and 122h (increased electrical resistance) are paired on a second side of the second Wheatstone bridge 142, in an opposite configuration, a fourth voltage can be outputted. Due to the opposite configuration, the third voltage has the same magnitude as the fourth voltage, but has a different polarity. This results in a positive voltage differential between the third voltage and the fourth voltage, and subsequently a positive voltage output.

Of course, the second Wheatstone bridge 142 could also be configured to generate a positive load output in the direction 134 and a negative load output in the direction 130. Although four strain gauges are shown in FIG. 12, two or more strain gauges can be used instead. In such a case, other types of resistors, having a fixed or variable resistance, can be used to replace the strain gauges, and the strain gauges can be arranged into circuits other than a Wheatstone bridge such as a half bridge or voltage divider.

For the load and moment sensor 100 to be usable in a wide range of applications, it is often desirable that the load and moment sensor 100 have good side load rejection. In other words, the load output may avoid change appreciably when either moment is applied, or loads from a different direction than the single direction are applied. Likewise with a good side load rejection, the moment output may avoid change when either a load is applied, or moments on a different plane than the single plane are applied. Good side load rejection is important because in analyzing the gait cycle of a user, only certain movements are desirable for analysis. Thus, good side load rejection can improve the accuracy of the data output from the load and moment sensor 100, which in turn can improve the ability of the prosthetic leg to mimic the human gait. Good side load rejection for the load and moment sensor 100 is highly dependent on accurate placement of the strain gauges 122a-122h on the sensing element 102.

To ensure functionality and proper side load rejection, the strain gauges 122a-122d can be placed on specific locations of the sensing element 102. In one embodiment, the strain gauges 122a-122d are located on a plane parallel to the mounting surface 124 of the sensing element 102. In addition, the strain gauges 122a-122d are located at the same position relative to a centerline 126 of the sensing element 102 running between the front side 108 and the back side 110. That is, the distance between the strain gauge 122a and the centerline, the distance between the strain gauge 122b and the centerline, the distance between the strain gauge 122c and the centerline, and the distance between the strain gauge 122d and the centerline are equal to each other.

To ensure functionality and proper side load rejection, the strain gauges 122e-122h are located on the centerline 126 of the sensing element 102 running between the front side 108 and the back side 110. As seen in FIGS. 8 and 9, the strain gauges 122e and 122f are located on a plane parallel to the mounting surface 124 of the sensing element 102. That is, the strain gauges 122e and 122f are the same distance from the mounting surface 124.

Furthermore, as seen in FIG. 10, the strain gauges 122g and 122h are located at the same position relative to the centerline 128 of the sensing element 102 running between the first side 112 and the second side 114. The strain gauge 122g is placed at the position relative to the centerline 128 where the measured strain will be equal and opposite to the strain measured by the strain gauge 122e when a moment is applied in the single plane. In a similar manner, the strain gauge 122h is placed at a position relative to the centerline 128 where the measured strain will be equal and opposite to the strain measured by the strain gauge 122f when a moment is applied in the single plane.

The location of the strain gauges also provides additional advantages aside from side load rejection. For example, the load and moment sensor may be rated to a load of 1440 N [323.7 lb] and a moment of 135 Nm [99.6 ft-lb]. At this applied load the load output will be about 9 mV/V, and at this applied moment the moment output will be about 45 mV/V. This means the moment output is only about 5 times greater than the load output. In other words, usable load and moment measurement are possible with a single, compact sensor. This is achieved primarily by the fact that the strain gauges 122a-122h are located at the extremities of the sensing element 102. If it was desired to further reduce the ratio of the moment output to the load output, then the strain gauges 122a-122h could be placed on the outside of the vertical walls rather than the inside, but this approach exposes the strain gauges 122a-122h and wiring to potential damage and may reduce the robustness of the design.

The present invention also offers additional advantages aside from side load rejection. Because the load and moment signals come from Wheatstone bridge circuits, the outputs of the load and moment sensor 100 have the well established benefits of this type of circuit. Namely, the output can be temperature compensated over a large operating temperature range, and the differential output is less susceptible to noise since the voltage differencing tends to subtract out the noise in the signal.

Furthermore, before the strain gauges 122a-122h are wired together, the sensing element 102 is coated in the area of the wiring with a layer of water proof insulating material such as epoxy. After the strain gauges 122a-122h are wired together, the strain gauges 122a-122h and wiring are encapsulated in a waterproof insulating material such as silicone. Thus, the load and moment sensor 100 is made dust and water resistant. The dust and water resistant properties of the load and moment sensor 100 allows the prosthetic leg to be more rugged and robust. The rugged and robust qualities enable the user to use the prosthetic leg in more dynamic settings where the prosthetic leg can be exposed to a variety of elements.

Besides the corrosion resistance as well as the dust and water resistance already mentioned, the load and moment sensor 100 has other features that make it robust. First, as long as applied cyclic forces result in loads and moments less than or equal to the rated load and moment, the cycle life of the load and moment sensor 100 will be practically infinite. As mentioned before, the use of semiconductor gauges for the strain gauges 122a-122h allows the load and moment sensor 100 to be designed for relatively low strain in the region of the strain gauges 122a-122h. The strain in the region of the strain gauges 122a-122h is about 600 μstrain at the rated load and moment. The maximum strain in the sensing element 102 is only slightly greater than this. This means the stress in the sensing element 102 is always below the fatigue limit of the high strength stainless steel material used. This results in a practically infinite fatigue life of the sensing element 102. At the same time, the strain gauges can be rated to 2000 μstrain for cyclic loads. At 600 μstrain, the gauges themselves should also have a practically infinite fatigue life. Given all this, the main limiter to the cycle life of the load and moment sensor 100 is likely to be the cycle life of the bond between the strain gauges 122a-122h and the sensing element 102. The cycle life of the bond tends to be very good given that this has been the focus of years of research and development in the strain gauge industry.

Additionally, because of the low strain at the rated load and moment, the load and moment sensor 100 can withstand loads and moments three times the rated load and moment without damage. This is because at three times the rated load, the yield strength of the sensing element 102 will not be exceeded, and the rated limit of 3000 μstrain, strain for the strain gauges 122a-122h will not be exceeded.

The resistance of the load and moment sensor 100 to overload conditions can also be improved by "preconditioning" the load and moment sensor 100. This means that after the strain gauges 122a-122h are bonded to the sensing element 102, and before the strain gauges 122a-122h are wired into the balanced Wheatstone bridges, the load and moment sensor 100 is exposed to a loading condition that produces loads and moments 1.5-2.0 times greater than the rated load and moment. In this way any localized plastic deformation of the sensing element 102 or any movement between the strain gauges 122a-122h and the sensing element 102 due to imperfect bonding can be accounted for when the Wheatstone bridge is balanced.

According to embodiments, components, devices, and systems of the present disclosure may include, be part of, or capable of integration with other components, devices, and systems, such as integrated circuits, processors, memory storage devices, etc. Such enhancements may modify, store, review, analyze, or otherwise act on data provided by embodiments of the present disclosure.

According to embodiments, aspects and implementations of the present disclosure may be useful for analysis of a variety of actions, activities, events, and phenomena. For example, embodiments may be used to analyze the separate, simultaneous, or relative contributions of force and moment at a given point. Such information may be used to detect load and moments that approach the known limits of a system or device to avoid extension beyond said limits. Such information may also be used to determine appropriate action in response to adjust at least one of the load and the moment. By further example, embodiments may be used to collect information about activity and environment during a gait cycle. For example, the force along a length of a leg or prosthetic leg acting on a knee or prosthetic knee as well as the moment acting on the knee or the prosthetic knee may be sensed and utilized in a system or device to track, react to, or respond to such readings. Responses may include the application of settings in a prosthetic knee to facilitate improved mobility of a user.

The present invention can also be used, for example, with other prosthetic joints and parts of the body. For example, the load and moment sensor 100 can also be used with other prosthetic joints and parts of the body. For example, the load and moment sensor 100 can also be used with prosthetic wrist joints and/or prosthetic elbow joints in addition to prosthetic knees or prosthetic ankles. Also, the load and moment sensor 100 may also be beneficially used in other applications such as in orthotics. Furthermore, the load and moment sensor 100 has diverse application and can be used in other fields which require a compact and robust sensor to detect an applied load and an applied moment, such as in the field of robotics, and machinery, even when they do not relate to human movement.

According to embodiments, features of devices and methods of the present disclosure may provide several features. For example, a single sensor, the load and moment sensor 100 measures both the applied load along in a single direction and the applied moment in a single plane. Both outputs offer the benefits of a strain gauge Wheatstone bridge which include temperature compensated output and differential output. The load and moment sensor 100 can withstand loads and moments three times the rated moment and load without damage and without a change in the no-load output.

The load and moment sensor 100 can also withstand large side loads, including loads due to impact, without a change in the no-load output. Further benefits include the following: the moment signal is less than 5 times the load signal at the rated load and moment; corrosion resistance; dust and water resistance; good side load rejection; compact, one piece design; and practically infinite cycle life when cyclic loads and moments are less than or equal to the rated load and moment.

Figure 13:
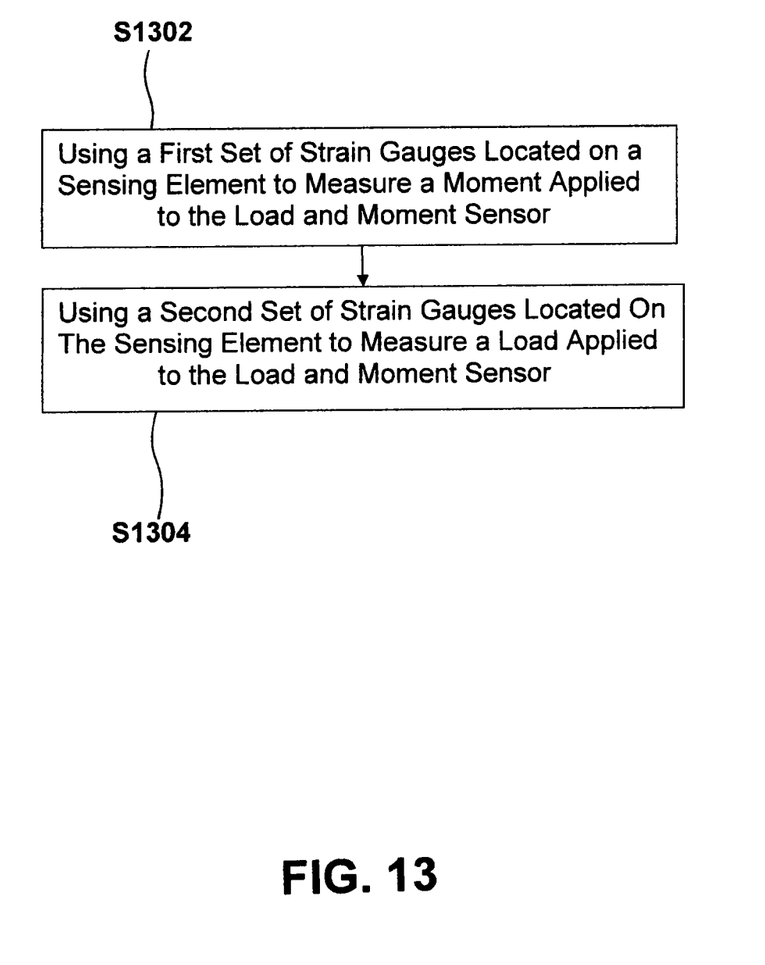
FIG. 13 depicts a process according to an embodiment of the present invention.

In one embodiment, the present invention includes a process as shown in FIG. 13. In Step S1302, a first set of strain gauges located on a sensing element are used to measure a moment applied to a load and moment sensor. For example, the strain gauges 122a-122d (FIGS. 8 and 9) located on the sensing element 102 can be used to measure a moment applied to the load and moment sensor 100 in a single plane. In Step S1304, a second set of strain gauges located on the sensing element are used to measure the load applied to the load and moment sensor. For example, the strain gauges 122e-122h (FIGS. 8-10) located on the sensing element 102 can be used to measure a load applied to the load and moment sensor 100 in a single direction. The outputs of the strain gauges 122a-122d can be part of the first Wheatstone bridge 140 (FIG. 11), while the outputs of the strain gauges 122e-122h can be part of the second Wheatstone bridge 142. In addition, the strain gauges 122a-122h can be located at specific locations as described above to allow for good side load rejection.

Those of ordinary skill would appreciate that the various illustrative logical blocks, modules, and algorithm steps described in connection with the examples disclosed herein may be implemented as electronic hardware, computer software, or combinations of both. Furthermore, the present invention can also be embodied on a machine readable medium causing a processor or computer to perform or execute certain functions.

To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosed apparatus and methods.

The various illustrative logical blocks, units, modules, and circuits described in connection with the examples disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the examples disclosed herein may be embodied directly in hardware, in a software module executed by a processor, or in a combination of the two. The steps of the method or algorithm may also be performed in an alternate order from those provided in the examples. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an Application Specific Integrated Circuit (ASIC). The ASIC may reside in a wireless modem. In the alternative, the processor and the storage medium may reside as discrete components in the wireless modem.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A load and moment sensor comprising:
a sensing element;
a first resistor circuit including a first plurality of strain gauges located on the sensing element, wherein the first resistor circuit provides an output representing a moment in a single plane; and
a second resistor circuit including a second plurality of strain gauges located on the sensing element, the second plurality of strain gauges including a first strain gauge, a second strain gauge, a third strain gauge, and a fourth strain gauge, wherein a first voltage is generated using the first strain gauge and the third strain gauge, a second voltage is generated using the second strain gauge and the fourth strain gauge, and a first voltage differential between the first voltage and the second voltage is used to determine a load applied to the load and moment sensor, and wherein the output provided by the first resistor circuit is separate from the first differential voltage of the second resistor circuit.

2. The sensor of claim 1 wherein the first plurality of strain gauges includes a fifth strain gauge, a sixth strain gauge, a seventh strain gauge, and an eighth strain gauge.

3. The sensor of claim 2 wherein the sensing element includes a mounting surface, and the fifth strain gauge, the sixth strain gauge, the seventh strain gauge, and the eighth strain gauge are located on a plane parallel to the mounting surface.

4. The sensor of claim 1 wherein the output provided by the first resistor circuit represents a magnitude of a moment applied to the load and moment sensor.

5. The sensor of claim 2 wherein a third voltage is generated using the fifth strain gauge and the seventh strain gauge, a fourth voltage is generated using the sixth strain gauge and the eighth strain gauge, and a second voltage differential between the third voltage and the fourth voltage is used to determine a moment applied to the load and moment sensor.

6. The sensor of claim 1 wherein the sensing element includes a mounting surface and the first strain gauge, the second strain gauge, the third strain gauge, and the fourth strain gauge are located on a plane perpendicular to the mounting surface.

7. The sensor of claim 1 wherein the first voltage differential represents a magnitude of a load applied to the load and moment sensor.

8. The sensor of claim 1 wherein the first plurality of strain gauges and the second plurality of strain gauges include semiconductor strain gauges.

9. A load and moment sensor comprising:
a sensing element including a mounting surface;
a first Wheatstone bridge including
a first strain gauge,
a second strain gauge,
a third strain gauge, and
a fourth strain gauge,
wherein the first strain gauge, the second strain gauge, the third strain gauge, and the fourth strain gauge are located on the sensing element in a first plane parallel to the mounting surface, and the first Wheatstone bridge provides an output representing a moment in a single plane; and
a second Wheatstone bridge including
a fifth strain gauge,
a sixth strain gauge,
a seventh strain gauge, and
an eighth strain gauge,
wherein the fifth strain gauge, the sixth strain gauge, the seventh strain gauge, and the eighth strain gauge are located on the sensing element in a second plane perpendicular to the mounting surface, and
wherein a first voltage is generated using the fifth strain gauge and the seventh strain gauge, a second voltage is generated using the sixth strain gauge and the eighth strain gauge, and a first voltage differential between the first voltage and the second voltage is used to determine a load applied to the load and moment sensor, and wherein the output provided by the first Wheatstone bridge is separate from the first voltage differential of the second Wheatstone bridge.

10. The sensor of claim 9 wherein the output provided by the first Wheatstone bridge represents a magnitude of a moment applied to the load and moment sensor.

11. The sensor of claim 9 wherein a third voltage is generated using the first strain gauge and the third strain gauge, a fourth voltage is generated using the second strain gauge and the fourth strain gauge, and a second voltage differential between the third voltage and the fourth voltage is used to determine a moment applied to the load and moment sensor.

12. The sensor of claim 9 wherein the first voltage differential represents a magnitude of a load applied to the load and moment sensor.

13. The sensor of claim 9 wherein the first strain gauge, the second strain gauge, the third strain gauge, the fourth strain gauge, the fifth strain gauge, the sixth strain gauge, the seventh strain gauge, and the eighth strain gauge are semiconductor strain gauges.

14. A method for determining a load and a moment applied to a load and moment sensor comprising:
using a first plurality of strain gauges located on a sensing element to provide an output to measure a moment applied to the load and moment sensor; and
using a second plurality of strain gauges located on the sensing element to measure a load applied to the load and moment sensor in a single direction, the second plurality of strain gauges including a first strain gauge, a second strain gauge, a third strain gauge, and a fourth strain gauge, wherein a first voltage is generated using the first strain gauge and the third strain gauge, a second voltage is generated using the second strain gauge and the fourth strain gauge, and a first voltage differential between the first voltage and the second voltage is used to determine a load applied to the load and moment sensor, and
wherein the output provided by the first plurality of strain gauges is separate from the first voltage differential of the second plurality of strain gauges.

15. The method of claim 14 wherein the moment is in a single plane.

16. The method of claim 14 wherein the output provided by the first plurality of strain gauges represents a magnitude of the moment applied to the load and moment sensor.

17. The method of claim 14 wherein using the first plurality of strain gauges to measure the moment applied to the load and moment sensor includes generating a third voltage and a fourth voltage from the first plurality of strain gauges, and generating a second voltage differential between the third voltage and the fourth voltage to determine the moment applied to the load and moment sensor.

18. The method of claim 14, wherein the first voltage differential represents a magnitude of the load applied to the load and moment sensor.

* * * * *